United States Patent
Watanabe et al.

(10) Patent No.: US 7,328,065 B2
(45) Date of Patent: Feb. 5, 2008

(54) ELECTRIC STIMULATOR AND DEFIBRILLATOR

(75) Inventors: Jun Watanabe, Tokyo (JP); Tsutomu Wakabayashi, Tokyo (JP); Naoto Akiyama, Tokyo (JP); Masahiko Inomata, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 124 days.

(21) Appl. No.: 10/727,493

(22) Filed: Dec. 5, 2003

(65) Prior Publication Data

US 2004/0162588 A1 Aug. 19, 2004

(30) Foreign Application Priority Data

Dec. 6, 2002 (JP) ............................. P2002-354524

(51) Int. Cl.
*A61N 1/39* (2006.01)
(52) U.S. Cl. ......................................................... 607/7
(58) Field of Classification Search ................ 607/5–8, 607/27, 28; 600/523
See application file for complete search history.

(56) References Cited

U.S. PATENT DOCUMENTS

| | | | | |
|---|---|---|---|---|
| 3,886,950 A | * | 6/1975 | Ukkestad et al. .............. 607/5 |
| 4,316,472 A | * | 2/1982 | Mirowski et al. .............. 607/9 |
| 4,328,808 A | * | 5/1982 | Charbonnier et al. .......... 607/8 |
| 5,088,489 A | * | 2/1992 | Lerman ........................ 607/8 |
| 5,115,807 A | * | 5/1992 | Pless et al. .................... 607/8 |
| 5,243,975 A | * | 9/1993 | Alferness et al. .............. 607/7 |
| 5,249,573 A | | 10/1993 | Fincke et al. |
| 5,397,336 A | * | 3/1995 | Hirschberg et al. ............ 607/6 |
| 5,713,937 A | * | 2/1998 | Nappholz et al. ............. 607/30 |
| 5,725,560 A | * | 3/1998 | Brink ............................. 607/5 |
| 5,879,374 A | | 3/1999 | Powers et al. |
| 2002/0022867 A1 | | 2/2002 | Akiyama et al. |

FOREIGN PATENT DOCUMENTS

| | | |
|---|---|---|
| JP | 54-112589 A | 9/1979 |
| JP | 9-550798 | 1/1997 |
| JP | 2001-245992 A | 9/2001 |
| WO | 94/27674 A1 | 12/1994 |
| WO | 01/66182 A1 | 9/2001 |

* cited by examiner

*Primary Examiner*—Scott M. Getzow
(74) *Attorney, Agent, or Firm*—Sughrue Mion, PLLC

(57) ABSTRACT

A plurality of electrodes are adapted to be attached on a living body. An electric pulse is output through the electrodes as an electric stimulation to the living body. An analyzer is operable to detect a waveform of the electric pulse and to analyze a parameter of the waveform. A display displays the parameter together with one of the waveform and a model waveform which is an invariable waveform representative of the electric pulse.

15 Claims, 9 Drawing Sheets

ELECTRIC STIMULATOR AND DEFIBRILLATOR

BACKGROUND OF THE INVENTION

The invention relates to an electric stimulator for providing electrical stimulation to a living body, and more particularly, to a technique for displaying various waveforms such as a result of analysis of an electrical waveform output from a defibrillator.

Devices, such as a defibrillator or low-frequency therapy equipment, have hitherto been utilized in the field of medical care as electric stimulators for providing electrical stimulation to a living body.

Japanese Patent Publication No 2001-245992A (corresponding to U.S. Patent Application Publication 2002/0022867A1) discloses a technique characterized by an electrical circuit capable of outputting a multiphasic waveform as a waveform of electric stimulation output from a defibrillator.

The defibrillator is a device for resuscitating the heart of a patient whose heart is fibrillating by providing electrical stimulation (electric energy) to the patient. When the patient's heart has changed to fibrillation, the defibrillator must be capable of being put into operation immediately and providing electrical stimulation (i.e., electric energy) at an appropriate timing. For this reason, maintenance is required to ensure that the defibrillator is capable of outputting desired electrical stimulation even when not used for actual treatment.

When the defibrillator is used for actual treatment, it is desirable to be able to verify that an operation for outputting electrical stimulation is normal, during or after treatment.

Such a necessity also applies not only to the defibrillator, but also to another electric stimulator which provides electrical stimulation to a living body.

Japanese Patent Publication No. 54-112589A discloses a defibrillator which displays an output voltage waveform applied to a living body (cf., page 2, upper right column, lines 40-41 and FIG. 3). This technique enables checking of a voltage waveform output to the living body. However, specific values, such as electric energy, resistance existing between electrodes, and a time period during which the electric energy has been supplied, are unknown. Hence, there is no way of knowing whether or not an electric pulse applied to the patient in defibrillation is appropriate

SUMMARY OF THE INVENTION

It is therefore an object of the invention to provide an electric stimulator and a defibrillator which enable checking of appropriateness of an electric pulse by analyzing an output electric pulse and displaying an analysis result and a model waveform or output waveform.

In order to achieve the above object, according to the invention, there is provided an electric stimulator for applying electric stimulation to a living body, comprising:

a plurality of electrodes, adapted to be attached on the living body, and through which an electric pulse is output as the electric stimulation;

an analyzer, operable to detect a waveform of the electric pulse and to analyze a parameter of the waveform; and a display, which displays the parameter together with one of the waveform and a model waveform which is an invariable waveform representative of the electric pulse.

According to the invention, there is also provided an electric stimulator for applying electric stimulation to a living body, the electric stimulator comprising:

a plurality of electrodes, adapted to be attached on the living body, and through which an electric pulse is output as the electric stimulation;

an energy charging element, in which an electric energy to be supplied to the electrodes is charged, the energy charging element having terminals;

an analyzer, operable to detect a voltage waveform between the terminals as a waveform of the electric pulse to be output, and to analyze a parameter of the waveform; and a display, which displays the parameter together with one of the waveform and a model waveform which is an invariable waveform representative of the electric pulse.

In the above configurations, the analysis result can be ascertained while being compared with the actual waveform or the model waveform.

Preferably, the display displays an index mark corresponding to the parameter.

In such a configuration, the analysis result can be ascertained while being compared with the index mark provided with the waveform.

Preferably, the parameter includes at least one of a discharge start voltage of the electric pulse, an electric energy output by the electric pulse, a duration of the electric pulse and a resistance between the electrodes.

In such a configuration, information pertaining to the waveform of the electric pulse can be ascertained.

Preferably, the electric stimulator further comprises a storage, which stores at least one of the waveform and the parameter.

In such a configuration, the waveform data can be read later from the storage and ascertained.

Preferably, the electric stimulator further comprising: a plurality of housings, which respectively house the electrodes therein; and a resistor, connected between the housings such that terminals thereof are exposed at the housings. Here, the electrodes are electrically connected via the resistor in a case where the electrodes are housed in the housings.

In such a configuration, an electric pulse can be ascertained for maintenance purpose.

Preferably, the electric stimulator serves as a defibrillator.

According to the invention, there is also provided an electric stimulator for applying electric stimulation to a living body, the electric stimulator comprising:

a plurality of electrodes, adapted to be attached on the living body, and through which an electric pulse is output as the electric stimulation;

an analyzer, operable to detect a waveform of the electric pulse and to analyze a parameter of the waveform; and a display, which displays the parameter.

According to the invention, there is also provided an electric stimulator for applying electric stimulation to a living body, the electric stimulator comprising:

a plurality of electrodes, adapted to be attached on the living body, and through which an electric pulse is output as the electric stimulation;

an energy charging element, in which an electric energy to be supplied to the electrodes is charged, the energy charging element having terminals;

an analyzer, operable to detect a voltage waveform between the terminals as a waveform of the electric pulse to be output, and to analyze a parameter of the waveform; and a display, which displays the parameter.

BRIEF DESCRIPTION OF THE DRAWINGS

The above objects and advantages of the present invention will become more apparent by describing in detail preferred exemplary embodiments thereof with reference to the accompanying drawings, wherein:

FIG. 4 is an external view of the electric stimulator (defibrillator) of the

FIGS. 10A and 10B show electrical waveforms of the electric stimulator (defibrillator) of the invention, wherein FIG. 10A is a voltage waveform of a capacitor 104 and FIG. 10B is the waveform of a voltage developing between electrode pads.

DETAILED DESCRIPTION OF THE INVENTION

Preferred embodiments of an electric stimulator according to the invention will be described hereinbelow in detail with reference to the accompanying drawings while a defibrillator is taken as an example.

Figure 1:
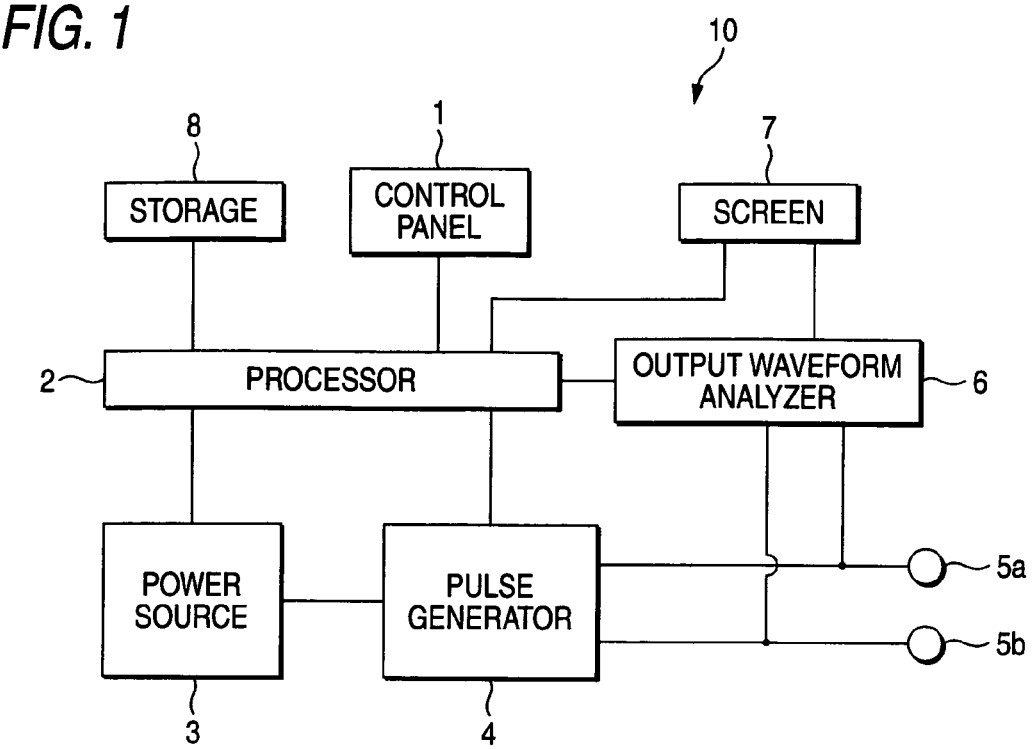
FIG. 1 is a constitutional block diagram showing an electric stimulator (defibrillator) according to the invention.

As shown in FIG. 1, in a defibrillator 10 according to one embodiment of the invention, a control panel 1 has several buttons to be used for performing operations for outputting an electric pulse for defibrillation treatment. When an operator has actuated these buttons, an instruction signal is output from the control panel 1 to a processor 2 in accordance with the operation.

Upon receipt of the instruction signal, the processor 2 outputs a signal to a power source 3 for instructing supply of the electric energy charged in the power source 3 to a pulse generator 4. As a result, the electric energy is supplied to the pulse generator 4. The processor 2 also outputs, to the pulse generator 4, a control signal for outputting an electric pulse to electrodes 5a, 5b (e.g., electrode paddles or the like).

Upon receipt of the control signal, the pulse generator 4 configures an electric pulse, to thereby output the thus-configured electric pulse to the electrodes 5a, 5b. The waveform pattern of the electric pulse may be a monophasic waveform, such as a damped sinusoidal curve or a truncated exponential curve used in a monophasic defibrillator, or a biphasic waveform such as a truncated exponential curve used in a biphasic defibrillator. Further, the waveform pattern may be a biphasic waveform or a multiphasic waveform in which a first-phase waveform and a second-phase waveform are alternately and repetitively iterated, as disclosed in Japanese Patent Publication No. 2001-245992A.

During a period in which the electric pulse is output to the electrodes 5a, 5b, an output waveform analyzer 6 detects a voltage waveform of the electric pulse, to thereby analyze the waveform of the electric pulse. A result of analysis is displayed on a screen 7.

A model waveform (described later) or the detected waveform is also displayed on the screen 7. The electric pulse and the analysis result are output from the output waveform analyzer 6 and stored in a storage 8 by way of the processor 2. As required, the analysis result and the electric pulse are read from the storage 8 and displayed on the screen 7 under the control of the processor 2, through the foregoing operations. Either the electric pulse or the analysis result may be stored in the storage 8.

Figure 2:
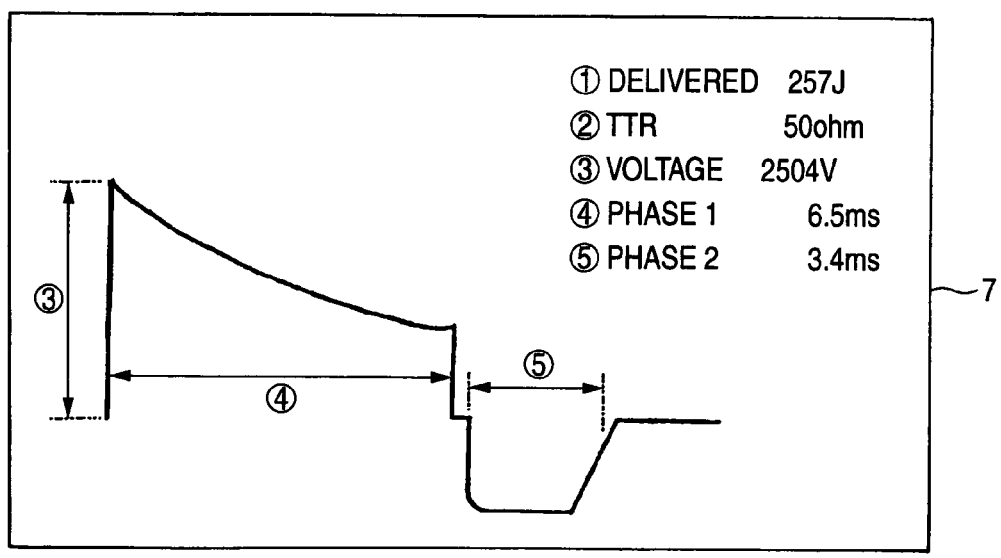
FIG. 2 is an example result of analysis of a waveform displayed on a screen in the electric stimulator (defibrillator) of the invention.

FIG. 2 shows an example in which a result of analysis of the electric pulse is displayed on the screen 7 when the defibrillator 10 outputs an electric pulse of biphasic waveform.

A model waveform is displayed on the left part of the screen 7. Characteristic values and other values pertaining to the shape of the voltage waveform detected and analyzed by the output waveform analyzer 6 are displayed on the right part of the screen 7. Displayed items are as follows.

"① Delivered" denotes the quantity of electric energy output from the electrodes 5a, 5b. "② TTR" denotes resistance existing between the electrodes 5a, 5b. "③ Voltage" denotes a voltage value obtained at the time of commencement of electrical discharge of a first-phase waveform output between the electrodes 5a, 5b. "④ Phase 1" denotes a duration of the first-phase waveform. "⑤ Phase 2" denotes a duration of a second-phase waveform.

Consequently, the detected pulse is analyzed in connection with items ① through ⑤ by the output waveform analyzer 6. Results of the analysis are displayed on the screen 7 on a per-item basis. In a case where the first phase waveform is produced as a result of discharge of the electric energy charged in a capacitor, computation of the resistance existing between the electrodes pertaining to "② TTR" can be performed on the basis of the capacitance of the capacitor, a discharge start voltage and discharge end voltage of the first-phase waveform, and a duration of the first-phase waveform. Computation of the amount of electric energy pertaining to "① Delivered" can be performed on the basis of the energy charged in the capacitor.

In relation to computation of the duration of the second-phase waveform defined in "⑤ Phase 2", the duration of the second-phase waveform is defined as a period from the time a second-phase amplitude has reached a predetermined percentage of the maximum amplitude until the time the amplitude is attenuated to the same predetermined percentage of the maximum amplitude.

Alternatively, the duration of the waveform may be determined by another method. For example, a control time to be used for outputting a second phase may be taken as a second-phase period. Internal resistance of the output waveform analyzer 6 is also taken into consideration at the time of these operations.

When the electric pulse has been output to the living body, "② TTR" corresponds to impedance of the living body. When the electric pulse has been output for maintenance to be described later, "② TTR" coincides with internal resistance housed between paddle holders 11a, 11b to be described later.

As described the above, the model biphasic waveform is also displayed on the screen 7. Index marks through ③ through ⑤ are provided with the model waveform so that the operator can visually comprehend meanings of the values ③ through ⑤.

Here, "③ Voltage" mans a voltage at which discharge of the first-phase waveform to be output between the electrodes 5a, 5b is to be started. For this reason, ③ is provided so as to indicate a waveform portion of the model waveform corresponding to the voltage at which discharge of the first-phase waveform is to be started. "④ Phase 1" means a duration of the first-phase waveform. ④ is provided so as to indicate a waveform portion of the model waveform corresponding to the duration of the first-phase waveform. "⑤ Phase 2" means a duration of the second-phase waveform. Hence, ⑤ is provided so as to indicate a waveform portion of the model waveform corresponding to the duration of the second-phase waveform.

In place of or in addition to the model waveform, the waveform of an electric pulse detected by the output waveform analyzer 6 may be displayed on the screen 7. As a result, the waveform of an electric pulse to be actually output can be visually checked, hereby enabling a check as to whether or not an output is normal. Incidentally, the above index marks may be provided with the waveform of an actual electric pulse.

Figure 3:
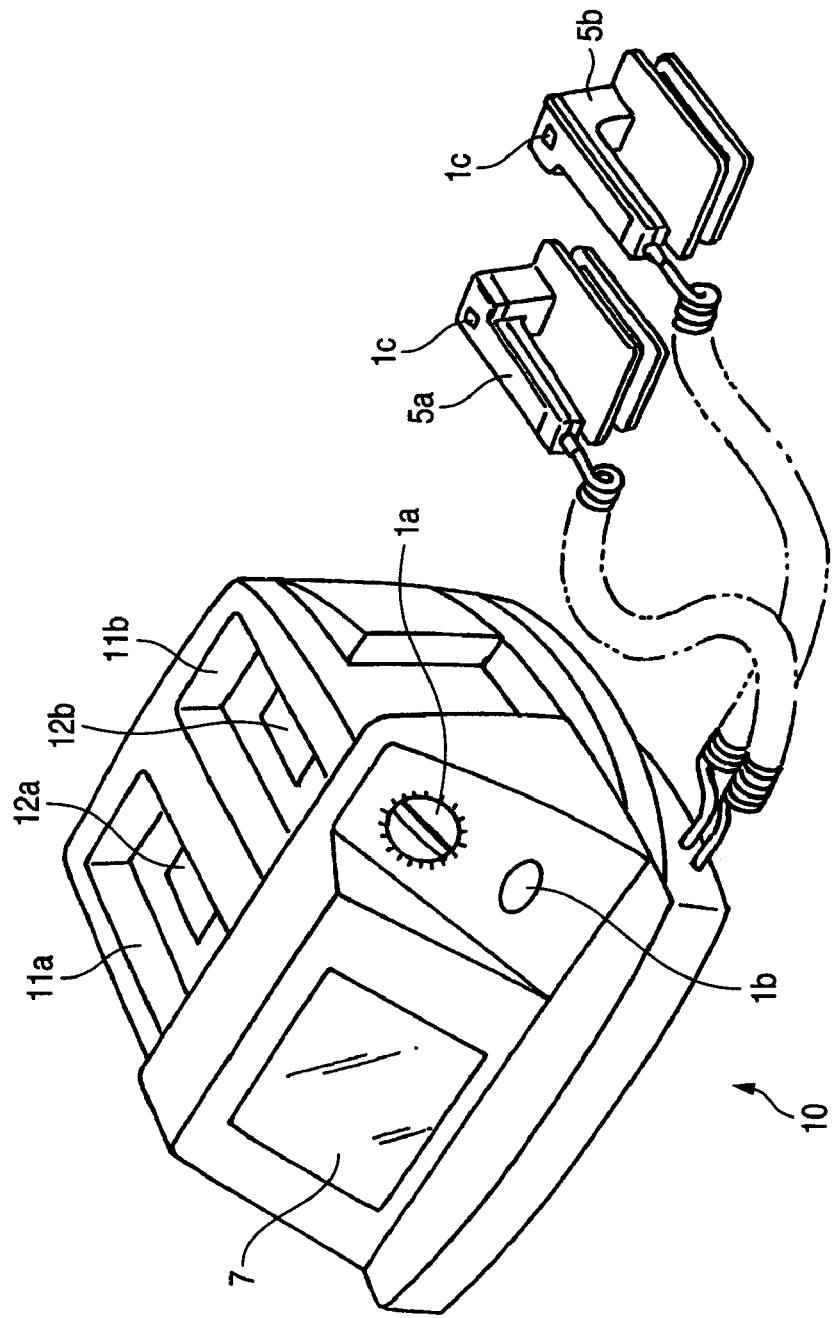
FIG. 3 is an external view of the electric stimulator (defibrillator) of the invention.
Figure 4:
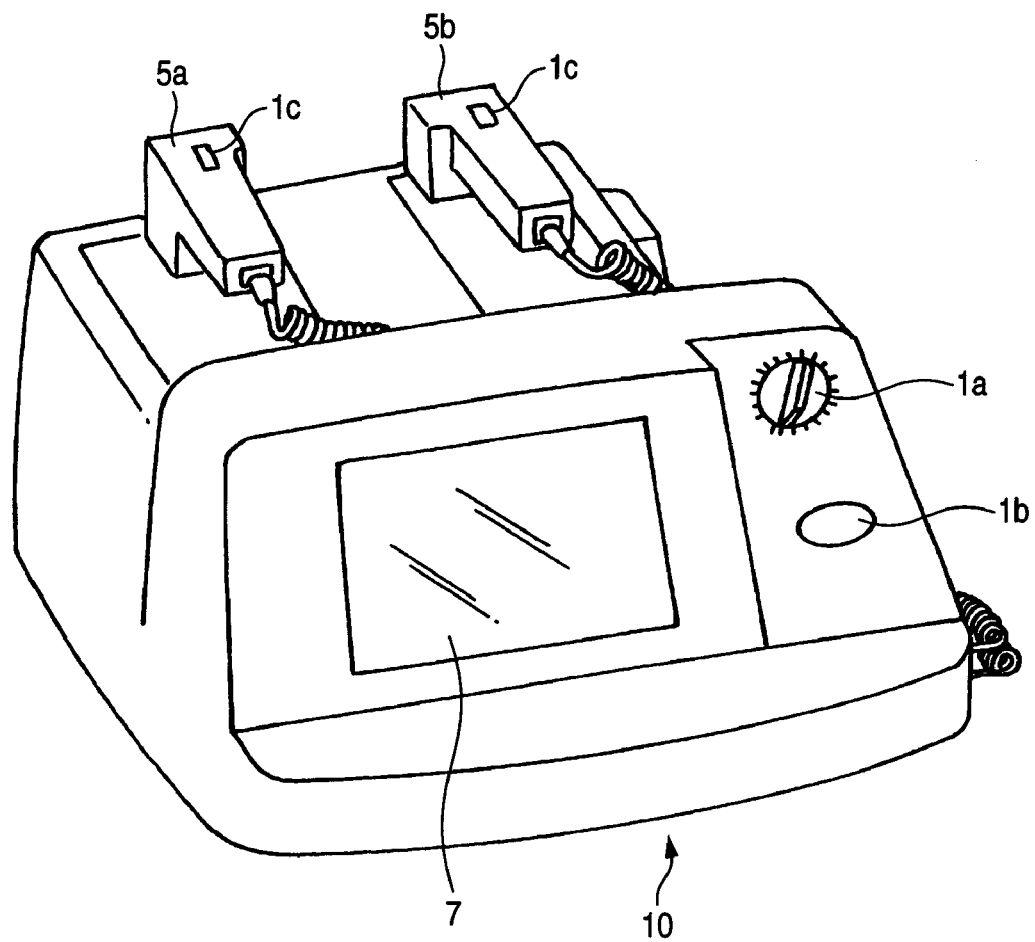

FIGS. 3 and 4 are external views of the defibrillator. A range selector 1a is to be used for controlling the quantity of electric energy of the electric pulse to be output. A button 1b is to be used for instructing the pulse generator 4 to be charged with electric energy supplied from the power source 3. A button 1c is to be used for instructing the electrode paddles 5a, 5b to output an electric pulse for defibrillation purpose. The range selector 1a and the buttons 1b, 1c belong to the control panel 1 shown in FIG. 1. The defibrillator 10 has paddle holders 11a, 11b for housing the electrode paddles 5a, 5b, respectively.

The structure of the defibrillator 10 required to test discharge of an electric pulse for maintenance will now be described. As shown in FIG. 3, a built-in resistor (not shown) is provided between the paddle holders 11a, 11b, and terminals 12a, 12b of the resistor are provided while being exposed in the respective paddle holders 11a, 11b.

Consequently, when the electrode paddles 5a, 5b are housed in the paddle holders 11a, 11b as shown in FIG. 4, the electrode paddles 5a, 5b come into contact with the terminals 12a, 12b. As a result, the electrode paddles 5a, 5b are electrically connected together by way of the built-in resistor.

In order to check the waveform of the electric pulse for maintenance purpose, an electric pulse is output between the electrode paddles 5a, 5b through actuation of the control panel 1 while the electrode paddles 5a, 5b are housed in the paddle holders 11a, 11b. The output waveform analyzer 6 is caused to analyze the electric pulse, and the result of analysis can be displayed on the screen 7.

When the electric pulse is being analyzed for maintenance purpose, a message "Basic Checks," for example, is displayed on the screen 7 by the processor 2. In contrast, when the electric pulse actually output for defibrillating a patient is being analyzed, a message "Actual Treatment," for example, is displayed on the screen 7 by the processor 2. Thus, the two cases may be distinguished from each other.

Moreover, there may be stored a mark or flag to be used for distinguishing a case where the electric pulse has been analyzed for maintenance by establishing a link to the electric pulse to be stored in the storage 8 and the analysis result thereof, from a case where the analysis result of the electric pulse actually output for defibrillating a patient has been made. As a result, when the stored data are read, the case for which the data have been acquired can be determined.

A time at which the electric pulse is output may be stored while being linked with the electric pulse to be stored in the storage 8 and the result of analysis thereof. As a result, when the stored data are read, a time at which maintenance has been performed or a time at which the defibrillation is performed can be checked.

A discharge test may be performed during the course of an operation to be performed daily for checking basic operations. The test result may be read from the storage 8 after completion of testing of all items and displayed on the screen 7. Storage of such data into the storage 8 is considerably important for verifying whether or not maintenance action and clinical treatment have been performed appropriately.

In this embodiment, as shown in FIG. 1, the output waveform analyzer 6 is designed to detect a voltage waveform developing between the electrodes 5a, 5b. However, the output waveform analyzer 6 may be an electrical element provided in the pulse generator 4 and may detect a voltage of an energy charging element (e.g., a capacitor) which temporarily charging the electric energy supplied from the power source 3.

Figure 5:
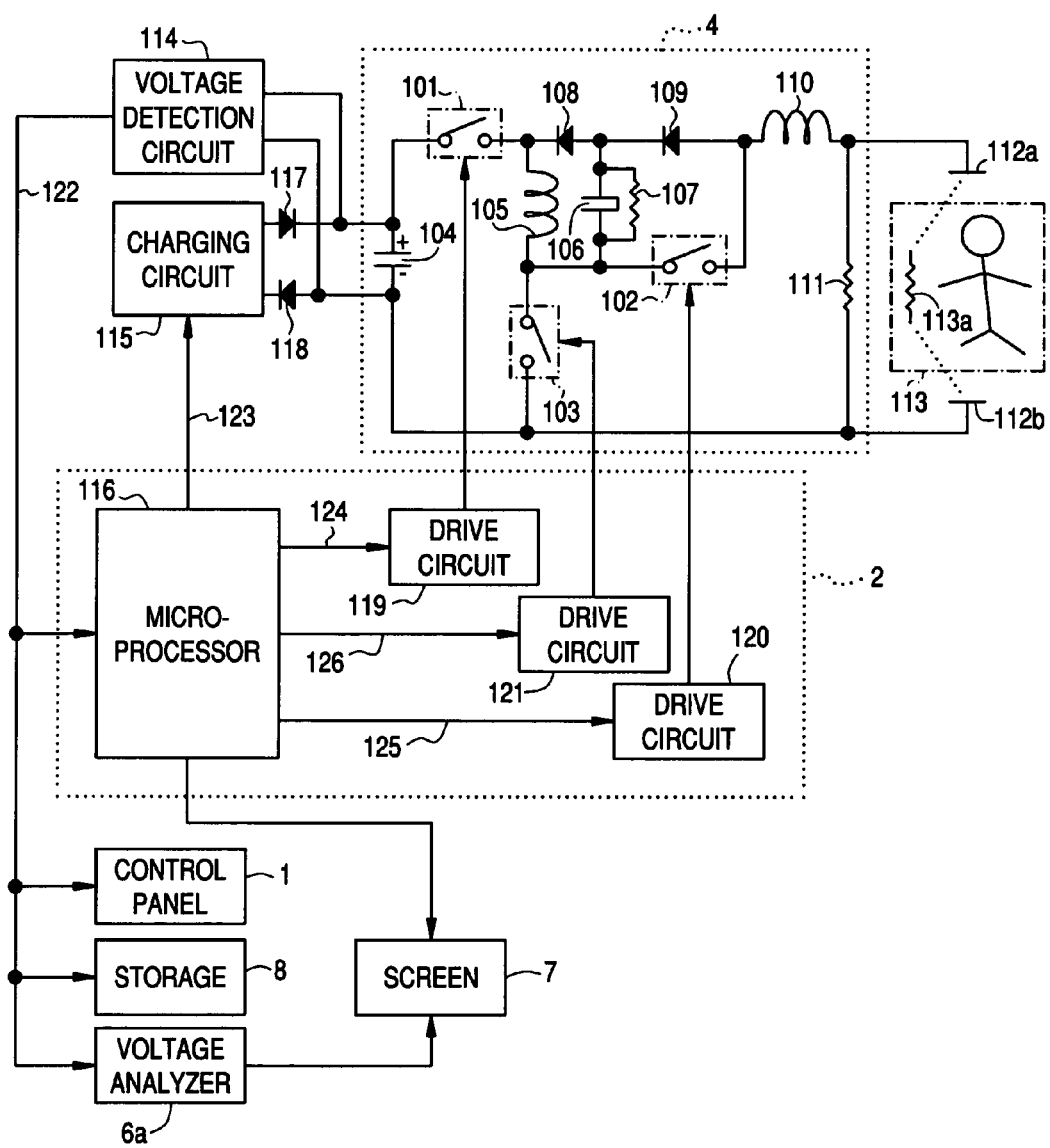
FIG. 5 is a constitutional block diagram showing the electric stimulator (defibrillator) according to the invention.

Such an example will be described with reference to an electrical circuit for outputting a biphasic waveform, which is disclosed in Japanese Patent Publication No. 2001-245992A. FIG. 5 shows a defibrillator employing the electrical circuit.

A positive terminal of the capacitor (energy charging element) 104 is connected to an inductor 105 by way of a switch 101. The other terminal of the inductor 106 is connected to the negative terminal of the capacitor 104 by way of a switch 103. The other terminal of the inductor 105 is also connected to one electrode paddle 112a for applying an electric pulse to a living body 113 (an impedance 113a of the living body), by way of an inductor 110 through a switch 102. Another electrode paddle 112b is connected to the negative terminal of the capacitor 104.

Diodes 108, 109 for preventing backflow of an electric current are connected in series between the switch 101 and the inductor 110, with the inductor 110 being taken as an anode side and the switch 101 being taken as a cathode side. The capacitor 106 and the resistor 107 for smoothing a waveform are interposed between the two diodes; that is, between the cathode of the diode 109 and a node which is located between the inductor 105 and the switch 102. Further, a protective resistor 111 is interposed between the electrode paddles 112a, 112b.

The capacitor 104 is charged by a charging circuit 115. Diodes 117, 118 for preventing backflow of an electric current are interposed between the respective electrodes of the capacitor 104 and the charging circuit 115. A voltage detection circuit 114 is connected across both electrodes of the capacitor 104, to thereby detect a voltage to be used for charging the capacitor 104. A voltage signal 122 for transmitting the thus-detected voltage is output to a microprocessor 116.

The voltage detected by the voltage detection circuit 114 is also transmitted to a capacitor voltage analyzer 6a as a voltage signal 122. The capacitor voltage analyzer 6a analyzes the received voltage signal 122, and the result of analysis is transmitted to and displayed on the screen 7. The voltage signal 122 is also transmitted to and stored in the storage 8. The result of analysis performed by the capacitor voltage analyzer 6a is also transmitted to and stored in the storage 8.

Connection is established such that opening and closing actions of the switches 101, 102, and 103 are respectively controlled by a drive circuit 119 of the switch 101, a drive circuit 120 of the switch 102, and a drive circuit 121 of the switch 10. The drive circuits 119, 120, and 121 are controlled by control signals 124, 125, and 126 output from the microprocessor 116. The microprocessor 116 controls the charging circuit 115 by a control signal 123.

Preferably, the switches 101, 102, and 103 are constituted of semiconductor switches formed from an insulated gate bipolar transistor (IGBT).

In FIG. 5, portions corresponding to the pulse generator 4 and the processor 2 are enclosed by dashed lines for reference purposes.

A method for controlling an output of electric pulse from the defibrillator will now be described. First, an operation for charging the capacitor 104 with electric energy will be described.

A charging start instruction is input to the microprocessor 116 (Step 1-1). The microprocessor 116 outputs control signals 124, 125, and 126 to drive circuits 119, 120, and 121 of the respective switches such that the switches 101, 102, and 103 become a continuous non-conductive state (Step 1-2). The switches 101, 102, and 103 become the continuous non-conductive state (Step 1-3).

The microprocessor 116 outputs a control signal 123 to the charging circuit 115 to start charging (Step 1-4). The charging circuit 115 starts charging the capacitor 104 with energy (Step 1-5). The microprocessor 116 receives the voltage signal 122 from the voltage detection circuit 114. When the voltage of the capacitor 104 detected by the voltage detection circuit 114 has increased to a predetermined voltage, the microprocessor 116 outputs a control signal 123 to the charging circuit 115 to stop charging (Step 1-6). The charging circuit 115 stops charging the capacitor 104 with energy (Step 1-7).

Figure 6:
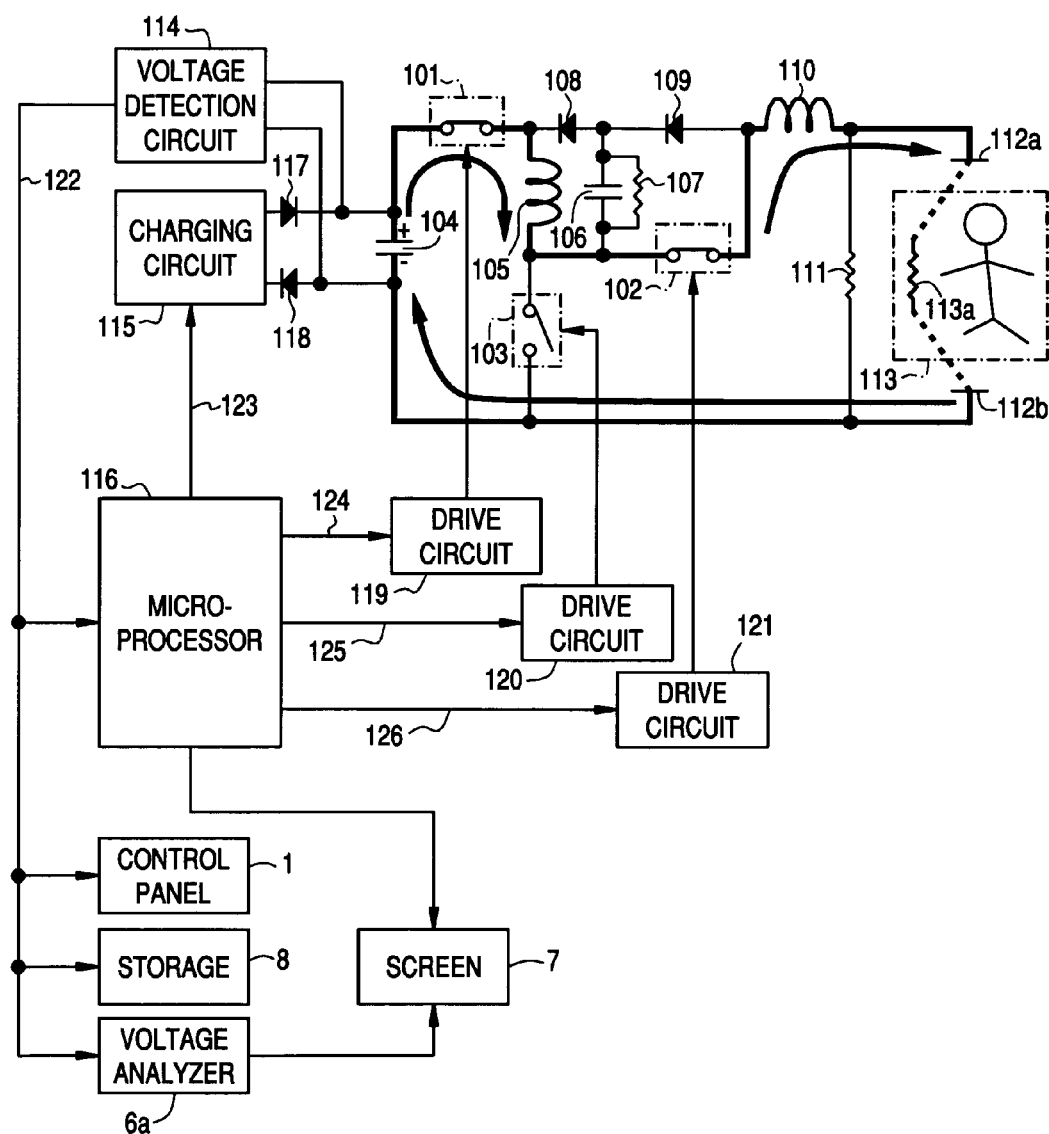
FIG. 6 is a descriptive view of an electrical path in the constitutional block circuit of the electric stimulator (defibrillator) of the invention employed when a positive-phase waveform is output.

Next, in relation to an operation for outputting electric energy to the electrode paddles 112a, 112b for applying an electric pulse from the capacitor 104 to the living body (patient) 113, an operation to be performed at the time of output of a positive-phase waveform will be described by reference to FIG. 6.

The discharge start instruction is input to the microprocessor 116 in response to the operator's action for pressing the button 1c of the control panel 1 to start discharging (Step 1-8). The microprocessor 116 outputs control signals 124, 126, and 126 to the switch drive circuits 119, 120, and 121 such that the switches 101 and 102 become a continuous conductive state and the switch 103 becomes a continuous non-conductive state (Step 1-9) The switches 101, 102 become a continuous conductive state, and the switch 103 becomes a continuous non-conductive state (Step 1-10). The voltage of the capacitor 104 decreases. Electric energy is supplied to the living body (patient) 113 in positive polarity (Step 1-11).

In accordance with a predetermined protocol, the microprocessor 116 outputs the control signals 124, 125, and 126 to the respective drive circuits 119, 120, and 121 such that the switches 101, 102 become a continuous non-conductive state and the switch 103 becomes a continuous conductive state, until the voltage of the capacitor 104 is attenuated to a predetermined percentage (e.g., 37%) of the initial voltage (Step 1-12). The switches 101 and 102 become a continuous non-conductive state, and the switch 103 becomes a continuous conductive state (Step 1-13). Output of electric energy (i.e., output of the positive-phase waveform) to the living body (patient) 113 is completed (Step 1-14).

Operation for outputting electric energy to the electrode paddles 112a, 112b for applying an electric pulse to the living body (patient) 113 from the capacitor 104 will now be described. Operation for outputting a negative-phase waveform will now be described by reference to FIGS. 7 through 9.

Figure 7:
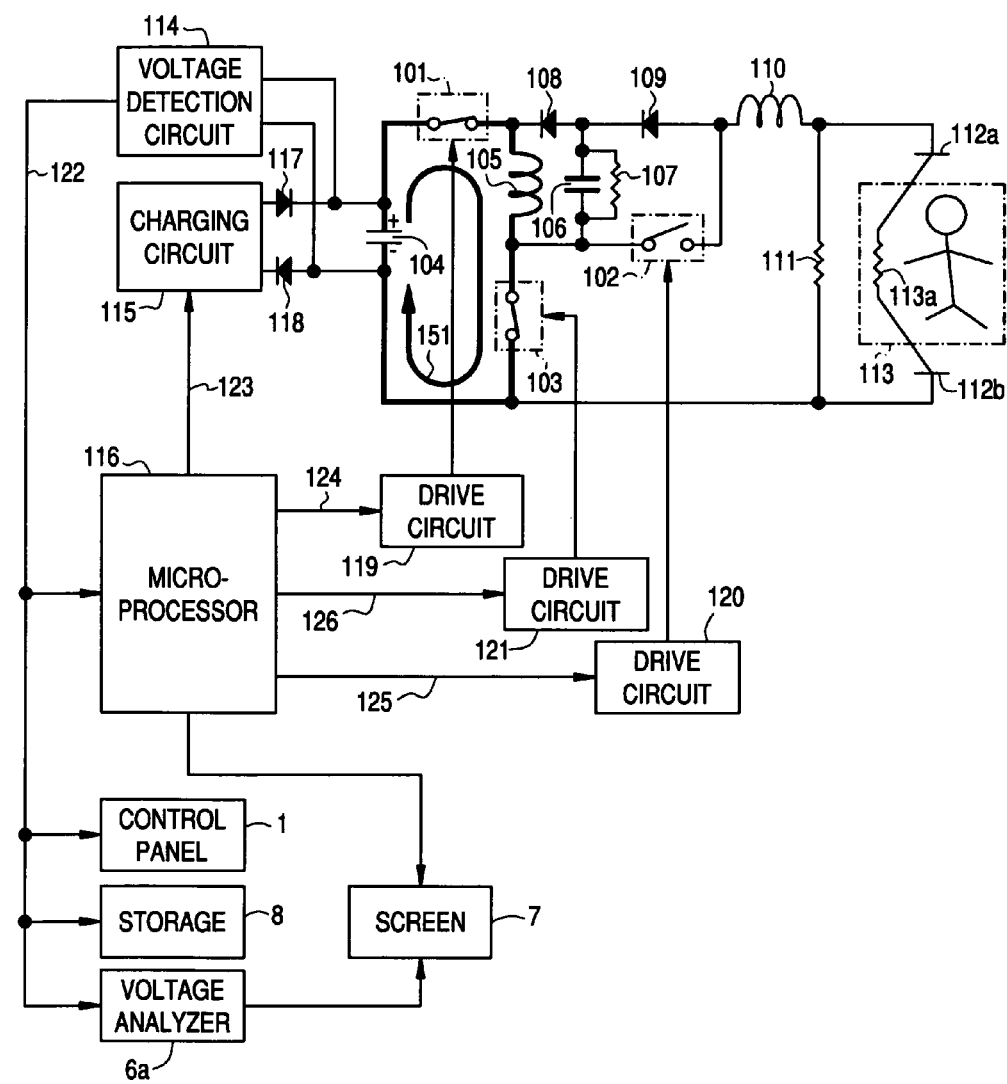
FIG. 7 is a descriptive view of an electrical path in the constitutional block circuit of the electric stimulator (defibrillator) of the invention employed when a switch 101 is in a conductive state at the time of output of a negative-phase waveform.

As shown in FIG. 7, when the switch 101 has become conductive (first time) at the time of output of the negative-phase waveform, an electrical current flows along a current path 151 designated by the arrow. The inductor 105 and the capacitor 104 constitute a closed circuit within the device without including the living body. At this time, the electric energy of the capacitor 104 is stored in the inductor 105 as magnetic energy as a result of flow of an electrical current through the current path 151. Electric energy is not output to the living body (patient) 113 during this step.

Figure 9:
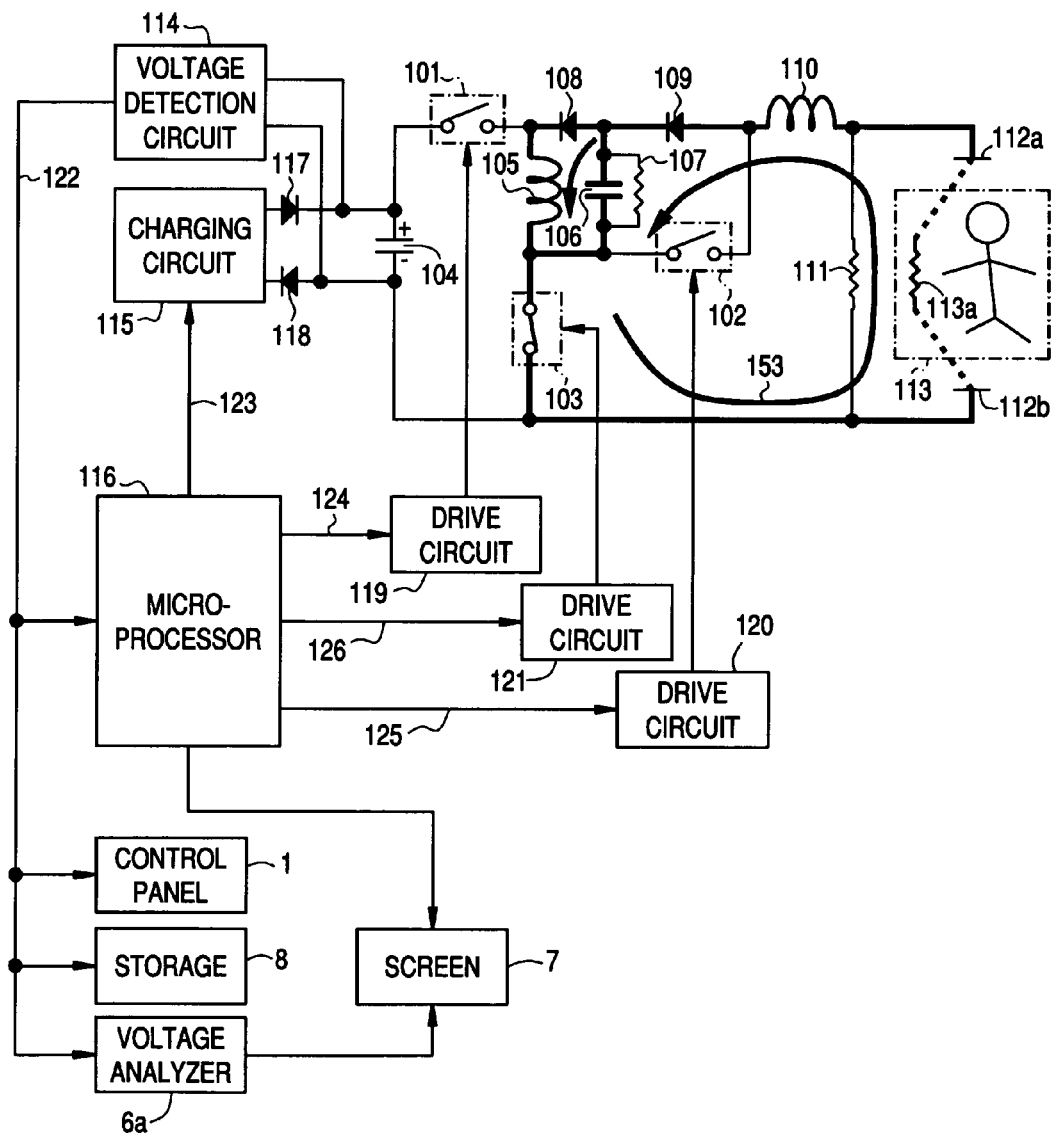
FIG. 9 is a descriptive view of an electrical path in the constitutional block circuit of the electric stimulator (defibrillator) of the invention employed when the switch 101 is in a non-conductive state at the time of output of the negative-phase waveform.

As shown in FIG. 9, when the switch 101 is in a non-conductive state at the time of output of the negative-phase waveform, the electric current flows along the current path 153 designated by the arrow. At this time the diodes 108 and 109 become conductive by a forward bias, whereupon the magnetic energy stored in the inductor 105 is output as electric energy. The electric current flows along the current path 153. As a result, there is achieved a state in which the electric energy is output to the living body (patient) 113. Concurrently, the electric current also flows into the capacitor 106, and consequently the electric energy is stored in the capacitor 106.

Figure 8:
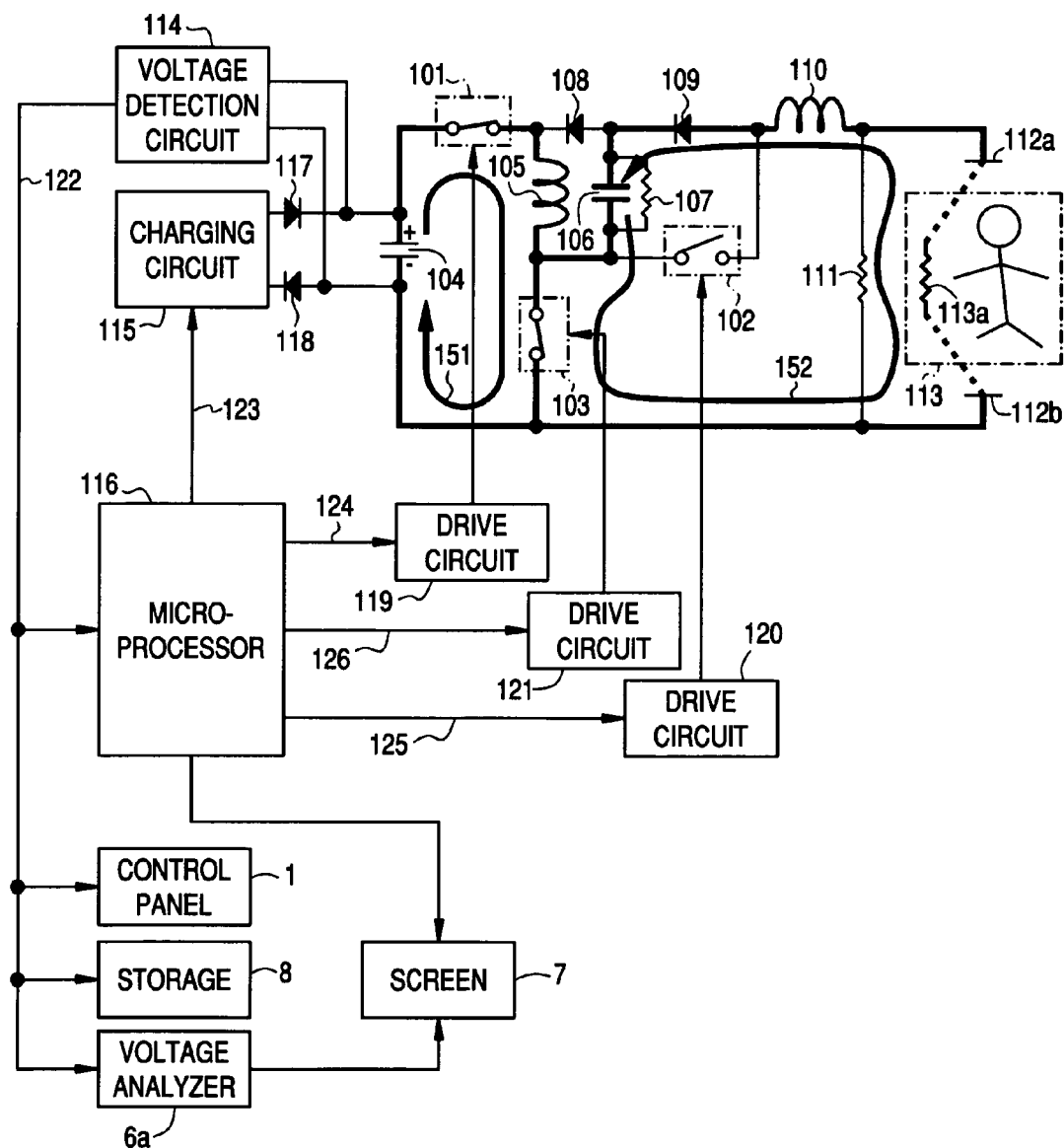
FIG. 8 is a descriptive view of an electrical path in the constitutional block circuit of the electric stimulator (defibrillator) of the invention employed when the switch 101 is in a conductive state at the time of output of the negative-phase waveform.

As shown in FIG. 8, when the switch 101 is conductive (second times or subsequent times) at the time of output of the negative-phase waveform, the electric current flows along the current paths 151, 152 designated by the arrows. At this time, the diode 108 is reversely biased and brought into a nonconductive state. The diode 109 remains in a conductive state by a forward bias. Consequently, the electric energy stored in the capacitor 106 is output, whereupon the electric current flows along the current path 152. As a result, there is maintained a state in which the electric energy is output to the living body (patient) 113. Simultaneously, as a result of flow of the electric current along the current path 151, the electric energy stored in the capacitor 104 is stored as magnetic energy in the inductor 105.

The microprocessor 116 outputs a control signal to the drive circuit 119 of the switch 101 for controlling on/off operation of the switch 101 so that an intended waveform can be output through use of a predetermined reference curve (Step 1-15). The switch 101 performs switching operation for repeating conduction/cutoff operation (Step 1-16). The voltage of the capacitor 104 decreases. Electric energy is supplied to the living body (patient) 113 in negative polarity (Step 1-17).

In accordance with a predetermined protocol, the microprocessor 116 outputs the control signal 124 to the drive circuit 119 of the switch 101 such that the switch 101 becomes a continuous non-conductive state (Step 1-18). The switch 101 becomes a continuous nonconductive state (Step 1-19). Output of the energy (i.e., the negative-phase-waveform output) to the living body (patient) 113 ends (Step 1-20).

Through these steps, the status of the current path of the circuit continues from that shown in FIG. 7, to that shown in FIG. 9, and to that shown in FIG. 8, by switching operation for causing the switch 101 to repetitively perform on/off operation. In subsequent steps, the status shown In FIG. 9 and that shown in FIG. 7 are repeated.

During the duration of the forgoing round of operations, the voltage waveform of the capacitor 104 detected by the voltage detection circuit 114 is analyzed by the capacitor voltage analyzer 6a. A result of analysis is displayed on the screen 7. Further, the analysis result is stored in the storage 8.

Figure 10A:
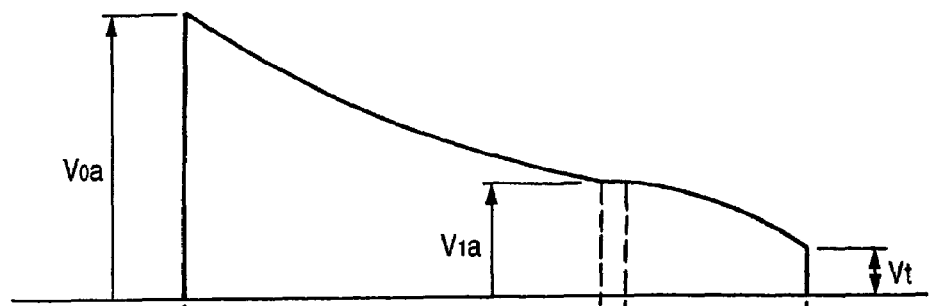

The voltage waveform of the capacitor 104 and a voltage waveform developing between the electrode paddles 112a, 112b will now be described by reference to FIGS. 10A and 10B. FIG. 10A Is a voltage waveform of the capacitor 104, and FIG. 10B shows a voltage waveform of the electrode paddles 112a, 112b.

Figure 10B:
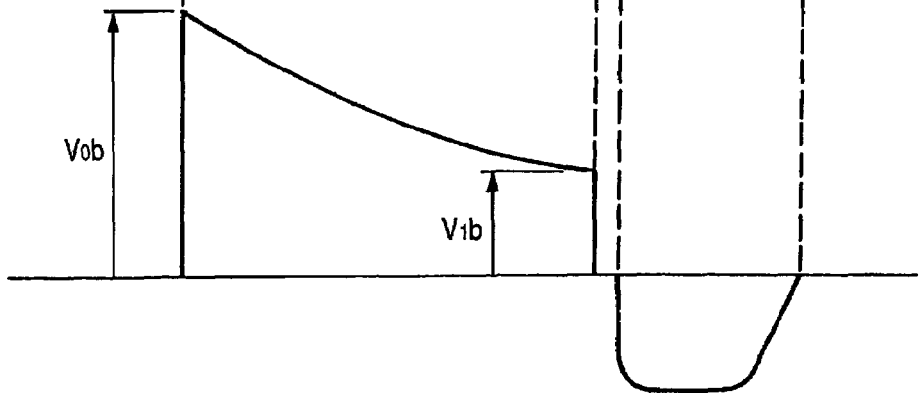

The voltage waveform developing during a first-phase period D1, which is depicted in both FIGS. 10A and 10B, is of a positive phase. The voltage waveform is attenuated in the manner of an exponential function from a voltage V0a to a voltage V1a and from a voltage V0b to a voltage V1b.

As shown in FIG. 10A, the voltage of the capacitor 104 is attenuated in a positive phase during a second-phase period D2. The voltage Vt is the voltage of the capacitor 104 obtained at the end of the second phase. As shown in FIG. 10B, a voltage between the electrode paddles assumes a negative phase.

A method for determining items shown in FIG. 2 from the voltage waveform of the capacitor 104 will now be described.

"④ Phase 1" designates the first-phase period D1, which can be determined from the time required to attenuate the voltage to a predetermined voltage level.

"⑤ Phase 2" designates the second-phase period D2, which can be determined from the time during which the microprocessor 116 has performed control operation for outputting an intended output waveform through use of a predetermined reference curve.

The voltage of the first-phase waveform obtained at the initiation of discharge is V0b. "③ Voltage" can be determined from a voltage V0a obtained at the time of initiation of discharge of the capacitor 104, in consideration of a voltage drop arising in another electrical element.

"② TTR" designates resistance developing between the electrode paddles, which can be determined by the following equation.

$$TTR = \left| -\frac{D1}{C} \frac{1}{\log V0a - \log V1a} - Rin \right| \quad (1)$$

Here,
D1: duration of the first phase
C: electrical capacitance of the capacitor 104
V0a: discharge start voltage of the capacitor 104 at the first phase
V1a: discharge end voltage of the capacitor 104 at the first phase
Rin: Internal resistance of a circuit "① Delivered" designates the quantity of output electric energy, which can be determined by the following equation.

$$Edelivered = \left( \frac{CV0a^2}{2} - \frac{CVt^2}{2} \right) \left( \frac{TTR}{TTR + Rloss} \right) \quad (2)$$

Here,
C: electrical capacitance of the capacitor 104
V0a: discharge start voltage of the capacitor 104 at the first phase
Vt: discharge end voltage of the capacitor 104 at the second phase
TTR: resistance between the electrode paddles 112a, 112b
Rloss: value determined by converting an internal loss of a circuit into resistance As shown in FIG. 2, the thus determined values are displayed on the screen 7. As mentioned above, the model waveform is displayed along with the index marks so that visual confirmation can be facilitated.

In the embodiment, the voltage detection circuit 114 detects the voltage of the capacitor 104. However, the voltage detection circuit 114 may detect and analyze the voltage developing between the electrode paddles 112a, 112b.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. An electric stimulator for applying electric stimulation to a living body, the electric stimulator comprising:
    a plurality of electrodes, adapted to be attached on the living body, and through which an electric pulse is output as the electric stimulation;
    an analyzer, operable to measure, during the output of the electric pulse from the electrodes, a continuous change of a voltage of the electric pulse which has been actually output from the electrodes, and to analyze a parameter of a waveform of the electric pulse, the analyzer being electrically connected to the electrodes without providing an inductor therebetween; and
    a display, which displays the parameter together with one of the waveform and a model waveform which is an invariable waveform representative of the electric pulse.

2. The electric stimulator as set forth in claim 1, wherein the display displays an index mark corresponding to the parameter.

3. The electric stimulator as set forth in claim 1, wherein the parameter includes at least one of a discharge start voltage of the electric pulse, an electric energy output by the electric pulse, a duration of the electric pulse and a resistance between the electrodes.

4. The electric stimulator as set forth in claim 1, further comprising a storage, which stores at least one of the waveform and the parameter.

5. The electric stimulator as set forth in claim 1, further comprising:
    a plurality of housings, which respectively house the electrodes therein; and a resistor, connected between the housings such that terminals thereof are exposed at the housings, wherein the electrodes are electrically connected via the resistor in a case where the electrodes are housed in the housings.

6. The electric stimulator as set forth in claim 1, wherein the electric stimulator serves as a defibrillator.

7. The electric stimulator as set forth in claim 1, wherein the waveform of the electric pulse is a monophasic waveform.

8. An electric stimulator for applying electric stimulation to a living body, the electric stimulator comprising:

a plurality of electrodes, adapted to be attached on the living body, and through which an electric pulse is output as the electric stimulation;

an energy charging element, in which an electric energy to be supplied to the electrodes is charged, the energy charging element having terminals;

an analyzer, operable to measure, during the output of the electric pulse from the electrodes, a continuous change of a voltage between the terminals as a waveform of the electric pulse which has been actually output from the electrodes, and to analyze a parameter of the waveform, the analyzer being electrically connected to the terminals of the energy charging element without providing an inductor therebetween; and a display, which displays the parameter together with one of the waveform and a model waveform which is an invariable waveform representative of the electric pulse.

9. The electric stimulator as set forth in claim 8, wherein the display displays an index mark corresponding to the parameter.

10. The electric stimulator as set forth in claim 8, wherein the parameter includes at least one of a discharge start voltage of the electric pulse, an electric energy output by the electric pulse, a duration of the electric pulse and a resistance between the electrodes.

11. The electric stimulator as set forth in claim 8, further comprising a storage, which stores at least one of the waveform and the parameter.

12. The electric stimulator as set forth in claim 8, further comprising:

a plurality of housings, which respectively house the electrodes therein; and a resistor, connected between the housings such that terminals thereof are exposed at the housings, wherein the electrodes are electrically connected via the resistor in a case where the electrodes are housed in the housings.

13. The electric stimulator as set forth in claim 8, wherein the electric stimulator serves as a defibrillator.

14. An electric stimulator for applying electric stimulation to a living body, the electric stimulator comprising:

a plurality of electrodes, adapted to be attached on the living body, and through which an electric pulse is output as the electric stimulation;

an analyzer, operable to measure, during the output of the electric pulse from the electrodes, a continuous change of a voltage of the electric pulse which has been actually output from the electrodes, and to analyze a parameter of a waveform of the electric pulse, the analyzer being electrically connected to the electrodes without providing an inductor therebetween; and a display, which displays the parameter.

15. An electric stimulator for applying electric stimulation to a living body, the electric stimulator comprising:

a plurality of electrodes, adapted to be attached on the living body, and through which an electric pulse is output as the electric stimulation;

an energy charging element, in which an electric energy to be supplied to the electrodes is charged, the energy charging element having terminals;

an analyzer, operable to measure, during the output of the electric pulse from the electrodes, a continuous change of a voltage between the terminals as a waveform of the electric pulse which has been actually output from the electrodes, and to analyze a parameter of the waveform, the analyzer being electronically connected to the terminals of the energy charging element without providing an inductor therebetween; and a display, which displays the parameter.

* * * * *